(12) United States Patent
Gaur et al.

(10) Patent No.: US 7,601,838 B2
(45) Date of Patent: Oct. 13, 2009

(54) 2-ALKYL/ARYL SULPHONYL-1,2,3,4-TETRAHYDRO-9H-PYRIDO (3,4-B) INDOLE-3-CARBOXYLIC ACID ESTERS/AMIDES USEFUL AS ANTITHROMBOTIC AGENTS

(75) Inventors: Stuti Gaur, Uttar Pradesh (IN); Zeeshan Fatima, Uttar Pradesh (IN); Anshuman Dixit, Uttar Pradesh (IN); Zahid Ali, Uttar Pradesh (IN); William Rascan Surin, Uttar Pradesh (IN); Kapil Kappor, Uttar Pradesh (IN); Kanta Bhutani, Uttar Pradesh (IN); Mohammed Salim Ansari, Uttar Pradesh (IN); Madhu Dikshit, Uttar Pradesh (IN); Anil Kumar Saxena, Uttar Pradesh (IN)

(73) Assignee: Council of Scientific and Industrial Research (IN)

( * ) Notice: Subject to any disclaimer, the term of this patent is extended or adjusted under 35 U.S.C. 154(b) by 517 days.

(21) Appl. No.: 11/023,915

(22) Filed: Dec. 28, 2004

(65) Prior Publication Data

US 2006/0142322 A1    Jun. 29, 2006

(51) Int. Cl.
C07D 471/04    (2006.01)
A61K 31/4353    (2006.01)

(52) U.S. Cl. ......................................... 546/81; 514/291
(58) Field of Classification Search ................... 546/81; 514/291
See application file for complete search history.

(56) References Cited

U.S. PATENT DOCUMENTS 6,720,330 B2 * 4/2004 Hay et al. ................... 514/292

FOREIGN PATENT DOCUMENTS

WO    9718194    * 5/1997

OTHER PUBLICATIONS

English Abstract Caplus DN 92:198594 Mohri Kunihiko et al., 1980.*
Caplus, English Abstract DN 106:138683, The formation and intramolecular acylation of . . . Harrison David et al 1986.*
Caplus English Abstract DN 112 : 76983, 1990.*
Caplus 117:171235 abstract IN 168420 Tripathi Ravish C., 1991.*
English Abstract, DN 128:13253, De Nanteuli et al, 1997.*

* cited by examiner

Primary Examiner—Rita J Desai
(74) Attorney, Agent, or Firm—Ostrolenk Faber LLP (57) ABSTRACT

The present invention relates to antithrombotic compounds 2-alkyl aryl sulphonyl-1,2,3,4-tetrahydro-9H-pyrido(3,4-b) indole-3-carboxylic acid esters/amides, pharmaceutically acceptable salts and compositions thereof to be used in the treatment of intravascular thrombosis such as myocardial ischemia and stroke. The compound has the following general structure

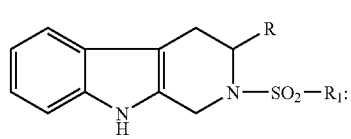

Formula 1 wherein R represents methyl ester or amide and $R_1$ represents alkyl, aryl and heteroaryl moiety.

24 Claims, 1 Drawing Sheet

Fig 1: Effect of Compound (i) on human platelet aggregation

Values are mean ± SEM (number of experiments =3 in each set)

2-ALKYL/ARYL SULPHONYL-1,2,3,4-TETRAHYDRO-9H-PYRIDO (3,4-B) INDOLE-3-CARBOXYLIC ACID ESTERS/AMIDES USEFUL AS ANTITHROMBOTIC AGENTS

FIELD OF THE INVENTION

The present invention relates to antithrombotic compounds 2-alkyl aryl sulphonyl-1,2,3,4-tetrahydro-9H-pyrido(3,4-b) indole-3-carboxylic acid esters/amides, pharmaceutically acceptable salts and compositions thereof useful in treatment of intravascular thrombosis such as myocardial ischemia and stroke. The compound has the following general structure Formula 1 wherein R represents methyl ester or amide and $R_1$ represents alkyl, aryl and heteroaryl moiety. The present invention particularly relates to novel compounds 2-alkyl/aryl sulphonyl-1,2,3,4-tetrahydro-9H-pyrido(3,4-b)indole -3-carboxylic acid esters/amides which are potent antithrombotic agents and can be useful in treatment of intravascular thrombosis, such as myocardial ischemia and stroke. The present invention also relates to processes for preparing the said novel compounds. More particularly the present invention relates to 2-alkyl/aryl sulphonyl-1,2,3,4-tetrahydro-9H-pyrido(3,4-b) indole-3-carboxylic acid esters/amides, processes for preps the said compounds and to their use in medicine.

BACKGROUND OF THE INVENTION AND PRIOR ART

Cardiovascular diseases associated with intravascular thrombosis are the most common cause of death in both developed and developing countries. Arterial and venous thromboses are the principal causes for the evolution of myocardial infarction, thromboembolic stroke and deep vein thrombosis. Approximately three million individuals die each year in the United States only from venous (deep vein thrombosis and pulmonary embolism) or arterial thrombosis (acute myocardial infarction and unstable angina).

Initiation of thrombosis is a complex process. The final event i.e. the thrombus formation, however, is primarily due to the activation of platelets and coagulation cascade. Clinical and experimental studies indicate that abnormalities in the normal blood flow, activation of platelets, coagulation cascade or fibrinolysis contribute to the pathogenesis of intravascular thrombosis/thromboembolism. Though the treatment strategy for thrombosis has improved with newer diagnostic and surgical tools but effective antithrombotic therapy with minimal side effects still poses a challenge to scientists around the globe.

Antithrombotic agents have been researched and developed for use in treating cardiovascular and other diseases. Presently established antithrombotic agents include heparin, coumarin, and aspirin. There are, however, limitations with these agents. For example, both heparin[1] and coumarin[2] have a highly-variable dose-related response, and their anticoagulant effects must be closely monitored to avoid a risk of serious bleeding. The erratic anticoagulant response of heparin is likely due to its propensity to bind non-specifically to plasma proteins. Aspirin has a limited efficacy and at high doses presents a risk of gastrointestinal bleeding.

Tissue plasminogen activators[3,4], platelet GPIIb/IIIa antagonists[5], ADP receptor antagonists[6], are also being currently used to treat thrombosis, however, these drugs have some inherent problems and limitations. Therefore, new search is taken up to develop next generation anti-thrombotic agents such as direct thrombin inhibitors[7], tissue factor pathway inhibitors[8], Factor Xa inhibitors[9], collagen antagonists[10] and gene therapy. The search of a potent orally active and specific anti-thrombotic agent with minimal danger of bleeding or unrelated side effects is thus an area of interest. Moreover, the high cost of anticoagulant and antithrombotic therapy necessitates the search for efficacious new chemical entities.

1. Circulation 1998, 98, 1575-82.
2. Drugs 1994, 48, 185-97.
3. J Intern Med 1994, 236, 425-32.
4. J Antibiot 1996, 49, 1014-21.
5. Current Pharmaceutical Design 2003, 9(28) 2317-2322.
6. Current Pharmaceutical Design 2003, 9(28) 2303-2316.
7. Expert Opinion on Investigational Drugs 2004, 13(5) 465-477.
8. Drugs News and Perspective 2003, 16(6) 363-369.
9. Current Pharmaceutical Design 2003, 9(28) 2337-23247.
10. Drugs of the future 2003 28(1), 61-67.

OBJECTS OF THE INVENTION

The main object of the invention is to provide novel molecules 2-alkyl/aryl sulphonyl-1,2,3,4-tetrahydro-9H-pyrido (3,4-b)indole-3-carboxylic acid esters/amides that exhibit better therapeutic efficacy to treat intravascular thrombosis, myocardial ischemia and stroke over the existing antithrombotic agents.

It is another object of the invention to provide novel 2-alkyl/aryl sulphonyl-1,2,3,4-tetrahydro-9H-pyrido(3,4b) indole-3-carboxylic acid esters/amides exhibiting activity against intravascular thrombosis for which there is/are no/few agent/agents available till date.

It is another object of the invention to provide 2-alkyl/aryl sulphonyl-1,2,3,4-tetrahydro-9H-pyrido(3,4-b)indole-3-carboxylic acid esters/amides as therapeutic agents for diseases arising out of alterations/impairment in intravascular thrombosis leading to myocardial ischemia and stroke.

It is another object of the invention to provide a process for preparing novel 2-alkyl/aryl sulphonyl-1,2,3,4-tetrahydro-9H-pyrido(3,4-b)indole-3-carboxylic acid esters/amides.

It is another object of the invention to provide a pharmaceutical composition comprising 2-alkyl/aryl sulphonyl-1,2, 3,4tetrahydro-9H-pyrido(3,4-b)indole-3-carboxylic acid esters/amides and pharmaceutically acceptable additive(s) and a process for preparing such composition.

It is another object of the invention to provide for the use of compounds of the present invention in the treatment or prevention of primary arterial thrombotic complications of atherosclerosis such as thrombotic stroke, peripheral vascular disease and myocardial infarction without thrombolysis.

It is another object of the invention to provide for the use of compounds of the invention for the treatment or prevention of arterial thrombotic complications due to interventions in atherosclerotic disease such as angioplasty, endarterectomy, stent placement, coronary and other vascular graft surgery.

It is another object of the invention to provide for the use of the compounds of the invention for the treatment or prevention of thrombotic complications of surgical or mechanical damage such as tissue salvage following surgical or accidental trauma, reconstructive surgery including skin flaps, and "reductive" surgery such as breast reduction.

It is another object of the invention to provide for the use of compounds of the present invention for the prevention of mechanically-induced platelet activation in vivo such as cardiopulmonary bypass (prevention of microthromboembolism), prevention of mechanically-induced platelet activation in vitro such as the use of the compounds in the preservation of blood products, e.g. platelet concentrates, prevention of shunt occlusion such as renal dialysis and plasmapheresis, thrombosis secondary to vascular damage/inflammation such as vasculitis, arteritis, glomerulonephritis and organ graft rejection.

It is another object of the invention to provide for the use of compounds of the present invention for the indicating with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

It is another object of the invention to provide for the use of compounds of the present invention for the treatment or prevention of venous thrombosis such as deep vein thrombosis, veno-occlusive disease, hematological conditions such as thrombocythemia and polycythemia, and migraine.

It is another object of the invention to provide for the use of compounds of the present invention in treatment of unstable angina, coronary angioplasty and myocardial infarction.

It is another object of the invention to provide for the use of compounds of the present invention for adjunctive therapy in the prevention of coronary arterial thrombosis during the management of unstable angina, coronary angioplasty and acute myocardial infarction, i.e. perithrombolysis.

It is another object of the invention to provide for a method of treating mammals to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

It is another object of the invention to provide for the use of compounds of the present invention in vitro to inhibit the aggregation of platelets in blood and blood products, e.g. for storage, or for ex vivo manipulations such as in diagnostic or research use.

It is another object of the invention to provide for the use of compounds of the present invention for the to inhibit platelet aggregation and clot formation in a mammal, especially a human, which comprises the internal administration.

It is another object of the invention to provide for the use of compounds of the present invention for the treatment of chronic or acute states of hyperaggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, which are likely to be responsive to these compounds.

It is another object of the invention to provide for the use of compounds of the present invention in a method for inhibiting the reocclusion of an artery or vein following fibrinolytic therapy, which comprises internal administration of compound and a fibrinolytic agent.

It is another object of the invention to provide for the use of compounds of the present invention for extracorporeal circulation, which is routinely used for cardiovascular surgery in order to oxygenate blood. Platelets adhere to surfaces of the extracorporeal circuit.

It is another object of the invention to provide for the use of compounds of the present invention for prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

To achieve the above and other objects the present invention provides novel pharmacologically active compounds, specifically new 2-alkyl aryl sulphonyl-1,2,3,4-tetrahydro-9H-pyrido(3,4-b)indole-3-carboxylic acid esters/amides which are used as potential therapeutic agents for intravascular thrombosis, myocardial ischemia and stroke and other disorders as mentioned above.

SUMMARY OF THE INVENTION

Accordingly the present invention relates to 2-alkyl/aryl sulphonyl-1,2,3,4-tetrahydro-9H-pyrido(3,4-b)indole-3-carboxylic acid esters/amides having formula 1:

Formula 1 wherein R is selected from methyl ester and amide; and $R_1$ is selected from the group consisting of alkyl aryl, and heteroaryl moiety.

In one embodiment of the invention, the compound comprises at least one of:
a. 2[-2,5dichlorobenzenesulfonyl]-1,2,3,4,-tetrahydro-9H-pyrido[3,4-b]indole-3-carboxylic acid ester
b. 2[2,4,6, trimethylbenzenesulfonyl]-1,2,3,4,-tetrahydro-9H-pyrido[3,4-b]indole-3-carboxylic acid ester
c. 2[2,nitrobenzenesulfonyl]-1,2,3,4,-tetrahydro-9H-pyrido[3,4-b]indole-3-carboxylic acid ester
d. 2[1-naphthylsulfonyl]-1,2,3,4,-tetrahydro-9H-pyrido[3,4-b]indole-3-carboxylic acid ester
e. 2-[4-methoxybenzenesulfonyl]-1,2,3,4,-tetrahydro-9H-pyrido[3,4-b]indole-3-carboxylic acid ester
f. 2[8-quinolinesulfonyl]-1,2,3,4,-tetrahydro-9H-pyrido[3,4-b]indole-3-carboxylic acid ester
g. 2-[dansylsulfonyl]-1,2,3,4,-tetrahydro-9H-pyrido[3,4-b]indole-3-carboxylic acid ester
h. 2[2,4,6 triisopropylbenzenesulfonyl]-1,2,3,4,-tetrahydro-9H-pyrido[3,4-b]indole-3-carboxylic acid ester
i. 2[4-fluorobenzenesulfonyl]-1,2,3,4,-tetrahydro-9H-pyrido[3,4-b]indole-3-carboxylic acid ester
j. 2[2-trifluoromethylbenzenesulfonyl]-1,2,3,4,-tetrahydro-9H-pyrido[3,4-b]indole-3-carboxylic acid ester
k. 2[methylsulfonyl]-1,2,3,4,-tetrahydro-9H-pyrido[3,4-b]indole-3-carboxylic acid ester
l. 2-[2-napthalenesulfonyl]-1,2,3,4,-tetrahydro-9H-pyrido[3,4-b]indole-3-carboxylic acid ester
m. 2[benzenesulfonyl]-1,2,3,4,-tetrahydro-9H-pyrido[3,4-b]indole-3-carboxylic acid ester n. 2[4-methylbenzenesulfonyl]-1,2,3,4,-tetrahydro-9H-pyrido[3,4b]indole-3-carboxylic acid ester In other embodiment the compound includes at least one of:

o. 2[-2,5 dichlorobenzenesulfonyl]-1,2,3,4,-tetrahydro-9H-pyrido[3,4-b]indole-3-carboxylic acid amide
p. 2[-4-methoxybenzenesulfonyl]-1,2,3,4,-tetrahydro-9H-pyrido[3,4-b]indole-3-carboxylic acid amide
q. 2[-1-naphthylsulfonyl]-1,2,3,4,-tetrahydro-9H-pyrido[3,4-b]indole-3-carboxylic acid amide
r. 2[8-quinolinesulfonyl]-1,2,3,4,-tetrahydro-9H-pyrido[3,4-b]indole-3-carboxylic acid amide
s. 2[-4-florobenzenesulfonyl]-1,2,3,4,-tetrahydro-9H-pyrido[3,4-b]indole3-carboxylic 2[-4-florobenzenesulfonyl]-1,2,3,4,-tetrahydro-9H-pyrido[3,4-b]indole3-carboxylic acid amide
t. 2[methanesulfonyl]-1,2,3,4,-tetrahydro-9H-pyrido[3,4-b]indole-3-carboxylic acid amide
u. 2[3-nitrobenzenesulfonyl]-1,2,3,4,-tetrahydro-9H-pyrido[3,4-b]indole-3-carboxylic acid amide
v. 2[2,4,6 trimethylbenzenesulfonyl-1,2,3,4,-tetrahydro-9H-pyrido[3,4-b]indole-3-carboxylic acid amide
w. 2-[2-naphthalenesulfonyl]-1,2,3,4,-tetrahydro-9H-pyrido[3,4-b]indole-3-carboxylic acid amide The present invention also provides a process for synthesis of 2-alkyl/aryl sulphonyl-1,2,3,4-tetrahydro-9H-pyrido(3,4-b)indole-3-carboxylic acid esters/amides of formula 1:

Formula 1 wherein R is selected from methyl ester and amide; and $R_1$ is selected from the group consisting of alkyl, aryl, and heteroaryl moiety, the process comprising condensing an alkyl or aryl sulphonyl chloride wherein aryl includes substituted phenyl substituted by group selected from the group consisting of hydrogen, halogens, alkyl and alkoxy, substituted napthyl substituted by group selected from the group consisting of hydrogen and dimethyl amino; and heteroaryl like quinoline with dimethyl-1,2,3,4-tetrahydro-9H-pyrido(3,4b)indole-3-carboxylate Formula 2 in the presence of a base and an organic solvent at temperature ranging from 30° C. to 120° C. for 8 to 24 hours to produce the corresponding 2-alkyl/aryl sulphonyl-1,2,3,4-tetrahydro-9H-pyrido(3,4-b)indole-3-carboxylic acid esters.

In another embodiment, the invention relates to a process for the synthesis of the above compounds by condensing an alkyl or aryl sulphonyl chloride where in aryl includes, substituted phenyl by groups like hydrogens, halogens, alkyl, alkoxy etc., substituted napthyl by hydrogen, di methyl amino, and heteroaryl like quinoline with dl 1,2,3,4-tetrahydro-9H-pyrido(3,4-b)indole-3-amide formula 3 in the presence of a base and an organic solvent at temperature ranging from 30° C. to 120° C. for 8 to 24 hours to produce the corresponding 2-alkyl/aryl sulphonyl-1,2,3,4-tetrahydro-9H-pyrido(3,4-b)indole-3-carboxylic acid amides.

In another embodiment, the invention relates to a process for the synthesis of the above compounds wherein 2-alkyl/aryl sulphonyl-1,2,3,4-tetrahydro-9H-pyrido(3,4-b)indole-3-carboxylic acid esters is treated with methanolic ammonia for 24 to 48 hours hrs to obtain the corresponding 2-alkyl/aryl sulphonyl-1,2,3,4-tetrahydro-9H-pyrido(3,4-b)indole-3-carboxylic acid amides.

In another preferred embodiment; the synthesis of 2-alkyl/aryl sulphonyl-1,2,3,4-tetrahydro-9H-pyrido(3,4-b)indole-3-carboxylic acid esters/amide of formula 1 includes the presence of one of the organic solvent selected from a group of acetone, DMF, THF, dioxane, a base including at least one of TEA, $K_2CO_3$, $Na_2CO_3$, pyridine and a temperature of about 30° C. to 120° C. for 8 to 24 hours.

In another embodiment, the molar ratios of the substituted sulphonyl chloride to dl methyl-1,2,3,4-tetrahydro-9H-pyrido(3,4-b)indole-3-carboxylate/dl 1,2,3,4-tetrahydro-9H-pyrido(3,4-b)indole-3-amide is about 1:2. In yet another preferred embodiment the organic solvents include acetone, DMF, THF, dioxane and the organic solvent is present about 0.8-2.2 ml per mmol.

In another embodiment, the molar ratio of the base to the dl methyl-1,2,3,4-tetrahydro-9H-pyrido(3,4-b)indole-3-carboxylate/dl 1,2,3,4-tetrahydro-9H-pyrido(3,4-b)indole-3-amide is about 1:4.

The invention also relates to pharmaceutical compositions having the compound of formula 1 described above in a mixture with a pharmaceutically acceptable carrier. The invention further relates to a process for preparing the pharmaceutical composition by bringing the compound into association with a pharmaceutically acceptable additive.

The invention also relates to method of treating various diseases with the pharmaceutical compositions of the present invention. In one embodiment, the method involves treating intravascular thrombosis in mammals by administering to a patient in need thereof a therapeutically effective amount of the pharmaceutical composition. In one embodiment, the method involves treating myocardial ischemia in mammals, by administering to a patient in need thereof a therapeutically effective amount of the pharmaceutical composition. In one embodiment, the method involves treating stroke in mammals, by administering to a patient in need thereof a therapeutically effective amount of the pharmaceutical composition.

In a preferred embodiment, the diseases treated are selected to be intravascular thrombosis, myocardial ischemia and stroke or a combination thereof. In another preferred embodiment the intravascular diseases are selected to include as mentioned above. In another preferred embodiment halogen of the compound is selected from the group of chlorine, bromine fluorine and iodine, and mixtures thereof, the alkoxy is selected to be a $C_1$-$C_{10}$ oxy, the alkyl is selected to be $C_1$-$C_{10}$ alkyl, and the heteroaryl is selected to be a $C_4$-$C_{10}$ heteroaryl.

DETAILED DESCRIPTION OF THE INVENTION

The compound of the present invention achieves the following objects:
i) providing novel molecules 2-alkyl aryl sulphonyl-1,2,3,4-tetrahydro-9H-pyrido(3,4-b)indole-3-carboxylic acid esters/amides that may exhibit better therapeutic efficacy to treat intravascular thrombosis, myocardial ischemia and stroke over the existing antithrombotic agents.

ii) providing novel 2-alkyl/aryl sulphonyl-1,2,3,4-tetrahydro-9H-pyrido(3,4-b)indole-3-carboxylic acid esters/amides exhibiting activity against intravascular thrombosis for which there is/are no/few agent/agents available till date to the best of the applicants knowledge.

iii) providing 2-alkyl/aryl sulphonyl-1,2,3,4-tetrahydro-9H-pyrido(3,4-b)indole-3-carboxylic acid esters/amides as therapeutic agents for the diseases arising out of alterations/impairment in intravascular thrombosis leading to myocardial ischemia and stroke.

iv) providing processes for preparing novel 2-alkyl/aryl sulphonyl-1,2,3,4-tetrahydro-9H-pyrido(3,4-b)indole-3-carboxylic acid esters/amides.

v) providing a pharmaceutical composition comprising 2-alkyl/aryl sulphonyl-1,2,3,4-tetrahydro-9H-pyrido(3,4-b)indole -3-carboxylic acid esters/amides. And pharmaceutically acceptable additive(s) and a process for preparing such composition.

vi) providing for use of the compounds in the treatment or prevention of primary arterial thrombotic complications of atherosclerosis such as thrombotic stroke, peripheral vascular disease, and myocardial infarction without thrombolysis.

vii) providing for the use of the compounds of the invention for the treatment or prevention of arterial thrombotic complications due to interventions in atherosclerotic disease such as angioplasty, endarterectomy, stent placement, coronary and other vascular graft surgery.

viii) providing for the use of the compounds of the invention for the treatment or prevention of thrombotic complications of surgical or mechanical damage such as tissue salvage following surgical or accidental trauma, reconstructive surgery including skin flaps, and "reductive" surgery such as breast reduction.

ix) providing for the use of the compounds of the invention for the prevention of mechanically-induced platelet activation in vivo such as cardiopulmonary bypass (prevention of microthromboembolism), prevention of mechanically-induced platelet activation in vitro such as the use of the compounds in the preservation of blood products, e.g. platelet concentrates, prevention of shunt occlusion such as renal dialysis and plasmapheresis, thrombosis secondary to vascular damage/inflammation such as vasculitis, arteritis, glomerulonephritis and organ graft rejection.

x) providing for the use of the compounds of the invention as indicators with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

xi) providing for the use of the compounds of the invention for the treatment or prevention of venous thrombosis such as deep vein thrombosis, veno-occlusive disease, hematological conditions such as thrombocythemia and polycythemia, and migraine.

xii) providing for the use of the compounds of the invention for the treatment of unstable angina, coronary angioplasty and myocardial infarction.

xiii) providing for the use of the compounds of the invention for the adjunctive therapy in the prevention of coronary arterial thrombosis during the management of unstable angina, coronary angioplasty and acute myocardial infraction, i.e. perithrombolysis. Agents commonly used for adjunctive therapy in the treatment of thrombotic disorders can be used, for example heparin and/or aspirin, just to mention a few.

xiv) providing for the use of the compounds of the invention for a method of treating mammals to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

xv) providing for the use of the compounds of the invention for the in vitro to inhibit the aggregation of platelets in blood and blood products, e.g. for storage, or for ex vivo manipulations such as in diagnostic or research use. This invention also provides a method of inhibiting platelet aggregation and clot formation in a mammal, especially a human, which comprises the internal administration.

xvi) providing for the use of the compounds of the invention for treatment of chronic or acute states of hyperaggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, which are likely to be responsive to these compounds.

xvii) providing for the use of the compounds of the invention in a method for inhibiting the reocclusion of an artery or vein following fibrinolytic therapy, which comprises internal administration of compound and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule.

xviii) providing for use of the compounds of the invention for extracorporeal circulation, which is routinely used for cardiovascular surgery in order to oxygenate blood. Platelets adhere to surfaces of the extracorporeal circuit. Platelets released from artificial surfaces show impaired hemostatic function. Compounds of the invention can be administered to prevent adhesion.

xix) providing for the use of the compounds of the invention for other applications including prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

To achieve the above and other objects the present invention provides novel pharmacologically active compounds, specifically new 2-alkyl aryl sulphonyl-1,2,3,4-tetrahydro-9H-pyrido(3,4-b)indole-3-carboxylic acid esters/amides which are used as potential therapeutic agents for intravascular thrombosis, myocardial ischemia and stroke and other disorders as mentioned above.

The compound of the invention has the formula 1 wherein R represents methyl ester or amide and $R_1$ represents alkyl, aryl and heteroaryl moiety. Representative compounds include:

a. 2[-2,5 dichlorobenzenesulfonyl]-1,2,3,4,-tetrahydro-9H-pyrido[3,4-b]indole-3-carboxylic acid ester
b. 2[2,4,6, trimethylbenzenesulfonyl]-1,2,3,4,-tetrahydro-9H-pyrido[3,4-b]indole-3-carboxylic acid ester
c. 2[2, nitrobenzenesulfonyl]-1,2,3,4,-tetrahydro-9H-pyrido[3,4-b]indole-3-carboxylic acid ester
d. 2[1-naphthylsulfonyl]-1,2,3,4,-tetrahydro-9H-pyrido[3,4-b]indole-3-carboxylic acid ester
e. 2-4-methoxybenzenesulfonyl]-1,2,3,4,-tetrahydro-9H-pyrido[3,4-b]indole-3-carboxylic acid ester
f. 2[8-quinolinesulfonyl]-1,2,3,4,-tetrahydro-9H-pyrido[3,4-b]indole-3-carboxylic acid ester
g. 2-[dansylsulfonyl]-1,2,3,4,-tetrahydro-9H-pyrido[3,4-b]indole-3-carboxylic acid ester
h. 2[2,4,6 triisopropylbenzenesulfonyl]-1,2,3,4,-tetrahydro-9H-pyrido[3,4-b]indole-3-carboxylic acid ester
i. 2[4-fluorobenzenesulfonyl]-1,2,3,4,-tetrahydro-9H-pyrido[3,4-b]indole-3-carboxylic acid ester
j. 2[2-trifluoromethylbenzenesulfonyl]-1,2,3,4,-tetrahydro-9H-pyrido[3,4-b]in-dole-3-carboxylic acid ester
k. 2[methylsulfonyl]-1,2,3,4,-tetrahydro-9H-pyrido[3,4-b]indole-3-carboxylic acid ester
l. 2-[2-naphthalenesulfonyl]-1,2,3,4,-tetrahydro-9H-pyrido[3,4-b]indole-3-carboxylic acid ester
m. 2[benzenesulfonyl]-1,2,3,4,-tetrahydro-9H-pyrido[3,4-b]indole-3-carboxylic acid ester
n. 2[4-methylbenzenesulfonyl]-1,2,3,4,-tetrahydro-9H-pyrido[3,4-b]indole-3-carboxylic acid ester
o. 2[-2,5-dichlorobenzenesulfonyl]-1,2,3,4,-tetrahydro-9H-pyrido[3,4-b]indole-3-carboxylic acid amide
p. 2[-4-methoxybenzenesulfonyl]-1,2,3,4,-tetrahydro-9H-pyrido[3,4-b]indole-3-carboxylic acid amide
q. 2[-1-naphthylsulfonyl]-1,2,3,4,-tetrahydro-9H-pyrido[3,4-b]indole-3-carboxylic acid amide
r. 2[8-quinolinesulfonyl]-1,2,3,4,-tetrahydro-9H-pyrido[3,4-b]indole-3-carboxylic acid amide
s. 2[-4-fluorobenzenesulfonyl]-1,2,3,4,-tetrahydro-9H-pyrido[3,4-b]indole-3-carboxylic acid amide
t. 2[methanesulfonyl]-1,2,3,4,-tetrahydro-9H-pyrido[3,4-b]indole-3-carboxylic acid amide
u. 2[3-nitrobenzenesulfonyl-1,2,3,4,-tetrahydro-9H-pyrido[3,4-b]indole-3-carboxylic acid amide
v. 2[2,4,6 trimethylbenzenesulfonyl-1,2,3,4,-tetrahydro-9H-pyrido[3,4-b]indole-3-carboxylic acid amide
W. 2-[2-naphthalenesulfonyl]-1,2,3,4,-tetrahydro-9H-pyrido[3,4-b]indole-3-carboxylic acid amide In the specification in formula 1, R designates methylester and amide $R_1$ designates alkyl group includes methyl, aryl group includes naphthyl and phenyl group substituted by alkyl, alkoxy, halogen groups and heteroaryl group includes quinoline.

A preferred group of compound comprises those in which R=methyl ester/amide and $R_1$=methyl, benzene, 4-methyl benzene, 2-naphthalene, 2,5dichlorobenzene, 2,4,6, trimethyl benzene, 2-nitrobenzene, 1-naphthyl, 4-methoxy benzene, 8-quinoline, dansyl, 2,4,6 triisopropyl benzene, 4-fluorobenzene, trifluoromethylbenzene.

The invention also provides a pharmaceutical composition comprising a compound of formula 1 in a mixture with a pharmaceutically acceptable conventional carriers and a process for the preparation of a pharmaceutical composition which comprises bringing a compound of the formula 1 into association with a pharmaceutically acceptable conventional carrier.

In addition, the invention provides a method of treating intravascular thrombosis and myocardial ischemia and stroke in mammals, that comprises administering to a subject in need thereof an effective amount of a compound of formula 1.

The compounds of the invention are useful in therapy, particularly in the prevention of platelet aggregation. The compounds of the invention have shown to possess anti-thrombotic activity in different test models. The compounds of the present invention are thus useful as anti-thrombotic agents, and are thus useful in the treatment or prevention of unstable angina, coronary angioplasty and myocardial infarction. The compounds prevent intravascular thrombosis, its progression or recurrence. They may be useful as additive or synergistic therapy to reduce the incidence of myocardial ischemia, acute myocardial infarction, unstable angina, during and after angioplasty or stent replacement, prevent cerebrovascular events, secondary prevention of stroke and pulmonary thromboembolism. These agents may also be used in combination with antithrombotic drugs and anticoagulants in patients undergoing angioplasty or stenting for coronary artery disease and also in conjunction with fibrinolysis protocols.

Diseases or conditions associated with platelet aggregation are disorders or procedures characterized by thrombosis, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, venous thrombosis, coronary arterial thrombosis, pathological effects of atherosclerosis and arteriosclerosis, platelet aggregation and clot formation in blood and blood products during storage, chronic or acute states of hyper-aggregability, reocclusion of an artery or vein following fibrinolytic therapy, platelet adhesion associated with extracorporeal circulation, thrombotic complications associated with thrombolytic therapy, thrombotic complications associated with coronary and other angioplasty, or thrombotic complications associated with coronary artery bypass procedures.

Disorders or procedures associated with thrombosis are unstable angina, coronary angioplasty, or myocardial infarction; said primary arterial thrombotic complications of atherosclerosis are thrombotic stroke, peripheral vascular disease, or myocardial infarction without thrombolysis; said thrombotic complications of interventions of atherosclerotic disease are angioplasty, endarterectomy, stent placement, coronary or other vascular graft surgery; said thrombotic complications of surgical or mechanical damage are associated with tissue salvage following surgical or accidental trauma, reconstructive surgery including skin flaps, or reductive surgery; said mechanically-induced platelet activation is caused by cardiopulmonary bypass resulting in microthromboembolism and storage of blood products; said shunt occlusion is renal dialysis and plasmapheresis; said thromboses secondary to vascular damage and inflammation are vasculitis, arteritis, glomerulonephritis or organ graft rejection; said indications with a diffuse thrombotic/platelet consumption component are disseminated intravascular coagulation, thrombotic thrombocytopenic purpura, hemolytic uremic syndrome, heparin-induced thrombocytopenia, or pre-eclampsia/eclampsia; said venous thrombosis are deep vein thrombosis, veno-occlusive disease, hematological conditions, or migraine; and said coronary arterial thrombosis is associated with unstable angina, coronary angioplasty or acute myocardial infarction.

Pathological effects of atherosclerosis and arteriosclerosis are arteriosclerosis, acute myocardial infarction, chronic stable angina, unstable angina, transient ischemic attacks, strokes, peripheral vascular disease, arterial thrombosis, preeclampsia, embolism, restenosis or abrupt closure following angioplasty, carotid endarterectomy, or anastomosis of vascular grafts; said chronic or acute states of hyper-aggregability is caused by DIC, septicemia, surgical or infectious shock, post-operative trauma post-partum trauma, cardiopulmonary bypass surgery, incompatible blood transfusion, abruptio placenta, thrombotic thrombocytopenic purpura, snake venom or immune diseases. A method of preparation of the inventive compounds consists of the condensation of different alkyl/aryl sulphonyl chlorides with dl methyl-1,2,3,4-tetrahydro-9H-pyrido(3,4-b)indole-3-carboxylate/dl-1,2,3,4-tetrahydro-9H-pyrido(3,4-b)indole-3-amide to get the compounds of formula 1 (2-alkyl/aryl sulphonyl-1,2,3,4-tetrahydro-9H-pyrido(3,4-b)indole-3-carboxylic acid esters/amides) as shown in scheme 1 of the accompanying drawings.

The compounds of the present invention can be used as pharmaceutical compositions comprising compounds of the present invention with a suitable pharmaceutical career. Preferably, these compositions are used to produce intravascular antithrombotic activity and contain an effective amount of the compounds useful in the method of the invention. The most preferred compounds of the invention are
1. 2[-2,5dichlorobenzenesulfonyl]-1,2,3,4-tetrahydro-9H-pyrido[3,4-b]indole-3-carboxylic acid ester.
2. 2[-4-methoxybenzenesulfonyl]-1,2,3,4,-tetrahydro-9H-pyrido[3,4-b]indole-3-carboxylic acid amide.
3. 2-[2-naphthalenesulfonyl]-1,2,3,4,-tetrahydro-9H-pyrido[3,4-b]indole-3-carboxylic acid amide.

The reaction leading to 2-alkyl/aryl sulphonyl-1,2,3,4-tetrahydro-9H-pyrido(3,4-b)indole-3-carboxylic acid esters/amides is shown in scheme 1 which represents the reaction sequence resulting in 2-alkyl aryl sulphonyl-1,2,3,4-tetrahydro-9H-pyrido(3,4-b)indole-3-carboxylic acid esters/amides, according to the present invention.

Scheme 1

It will be noted that according to the foregoing scheme the methods that lead to the synthesis of 2-alkyl/aryl sulphonyl-1,2,3,4-tetrahydro-9H-pyrido(3,4-b)indole-3-carboxylic acid esters/amides of formula 1 as shown earlier are as follows The method involves in the synthesis of the compounds of formula 1 wherein R is methyl ester comprises of condensation of an alkyl or aryl sulphonyl chloride with dimethyl-1,2,3,4-tetrahydro-9H-pyrido(3,4-b)indole-3-carboxylate of formula 2 in the presence of a base selected from trimethylamine, potassium carbonate, pyridine in organic solvent selected from THF, DMF, acetone, dioxane at a temperature ranging from 30° C. to 120° C. for 8 to 24 hours to produce the corresponding 2-alkyl/aryl sulphonyl-1,2,3,4-tetrahydro-9H-pyrido(3,4-b)indole-3-carboxylic acid esters.

Two methods were used for the synthesis of 2-alkyl/aryl sulphonyl-1,2,3,4-tetrahydro-9H-pyrido(3,4-b)indole-3-carboxylic acid amides.

The first method relates to a process for the synthesis of the above compounds by condensing a alkyl or aryl sulphonyl chloride with dl 1,2,3,4-tetrahydro-9H-pyrido(3,4-b)indole-3-amide formula 3 in the presence of a base selected from trimethylamine and an organic solvent DMF at temperature 30° C. to 120° C. for 8 to 12 hours to produce the corresponding 2-alkyl/aryl sulphonyl-1,2,3,4-tetrahydro-9H-pyrido(3,4-b)indole-3-carboxylic acid amide of formula 1 wherein R=CONH$_2$.

The second method involves 2-alkyl/aryl sulphonyl-1,2,3,4-tetrahydro-9H-pyrido(3,4-b)indole-3-carboxylic acid esters synthesized as described previously, treated with methanolic ammonia for 24-32 hours at 32° C. to obtain 2-alkyl/aryl sulphonyl-1,2,3,4-tetrahydro9H-pyrido(3,4-b)indole-3-carboxylic acid amide.

The compounds of the invention show marked antithrombotic activity and can be used as therapeutic agents for the treatment of intravascular thrombosis, myocardial ischemia and stroke as shown for instance by the following data of the compounds (i) 2-[2,5-dichlorobenzenesulfonyl]-1,2,3,4,-tetrahydro-9H-pyrido[3,4-b]indole-3-carboxylic acid ester,
(ii) 2-[4-methoxybenzenesulfonyl]-1,2,3,4,-tetrahydro9H-pyrido[3,4-b]indole-3-carboxylic acid amide.
(iii) 2-[2-naphthalenesulfonyl]-1,2,3,4,-tetrahydro-9H-pyrido[3,4-b]indole-3-carboxylic acid amide, Pharmacological Activity (1) Methods:

1.1 Effect on Mouse Thrombosis

Pulmonary thromboembolism was induced by following a method of Diminno and Silver[1]. Test compounds (30 µM/Kg) or vehicle were administered orally 60 min prior to the thrombotic challenge. A mixture of collagen (150 µg/ml) and adrenaline (50 µg/mL) was administered by the rapid intravenous injection into the tail vein to induce hind limb paralysis or death. A group of 10 animals were used to evaluate the effect of test compound, while 5 mice were used to assess effect of a standard drug, aspirin and a group of vehicle treated (n=5) mice was also used each experiment.

% Protection was expressed as:

$$\frac{(P_{control} - P_{test})}{P_{control}} \times 100$$

$P_{test}$ is the number of animals paralyzed/dead in the test compound-treated group, and $P_{control}$ is the number of animals paralyzed/dead in vehicle treated group.

1.2 Effect on mouse-tail Bleeding time: Mice tail bleeding time was performed by method of Dejna et al,[2]. The tail 2 mm from tip was incised and the blood oozed was soaked with filter paper till the bleeding stops. The time elapsed from the tip incision to the stoppage of bleeding was determined as the bleeding time. Test compound (30 µM/kg), aspirin or vehicle was given orally 60 min prior to the tail incision. Each group consisted of 5 mice.

1.3 Evaluation of compounds on platelet aggregation: Platelet aggregation was monitored according to the protocol described earlier[3]. Sprague Dawley rats (wt 250-300 gm) were anaesthetized with ether and blood (9 mL) was drawn from the heart into a plastic syringe containing 1 ml of 1.9% tri- Sodium citrate: The blood was centrifuged at 275×g for 20 min and the platelet rich plasma (PRP) was collect. The remaining blood was further centrifuged at 1500 g for 15 min at 20° C. to obtain platelet poor plasma (PPP). The platelet count in the PRP was adjusted to 2×10$^8$ cells/ml by using PPP. Adenosine-5'-diphosphate (ADP), thrombin, collagen, calcium ionophore A23187 or phorbol myristate ester (PMA) induced aggregation was monitored on a dual channel aggregometer (Chrono-log, USA). The test compound was incubated with PRP or 5 min before the addition of aggregation on inducing agent. Percent inhibition of the test compounds at various concentrations was calculated as follows:

$$\% \text{ Inhibition} = \frac{[Aggregation_{vehicle} - Aggregation_{test}]}{Aggregation_{vehicle}} \times 100$$

1.4 Evaluation of coagulation parameters: Blood was collected by cardiac puncture from ether-anaesthetized rat using a syringe containing 3.2% tri-sodium citrate (9:1, v/v). Plasma was obtained by centrifugation of citrated blood at 2500×g for 15 min at 20° C. Stock solutions of the test compounds were prepared freshly in DMSO and were diluted in DMSO. Thrombin time (TT), prothrombin time (PT) and activated partial thromboplastin time (aPTT) were evaluated according to manufacturer's instructions supplied with kits (Stago, France) and measured by Coagulometer (Stago, France)[4]. In each set of experiment effect of DMSO on these parameters was also assessed and was used to calculate change in TT, PT or aPTT.

1.5 Rabbit venous thrombosis model: Experiments were performed on New Zealand white strain rabbits (2-3 kg) either sex. *Escherichia coli* LPS strain 1055:B5 (Sigma Chemicals, USA) was injected intravenously via ear vein (1 µg/kg)[5,6]. Jugular veins on both sides were exposed and dissected free from surrounding tissue. Two loose surer were placed 1.5 cm apart and all collateral veins were ligated. Four hours after *E. coli* endotoxin injection (animal is watched for any signs of hypersensitivity reaction during this period), stasis was established and maintained for 45 min by tightening the two sutures. Ligated segments were removed and opened longitudinally and the thrombus was carefully removed and weighed. Heparin sodium (Beparine from beef intestinal mucosa ≧140 USP units/mg; Biological E. Limited, India) was given in doses of (0.5, 0.25, 0.1 mg/kg i.v., via ear vein) 5 min before stasis.

1.6 Effect of compound (i) on human platelet aggregation in vitro: Platelet aggregation study was done on human platelets following isolation of PRP from the human blood as described above (1.3). Aggregation was induced by collagen (10 µg/ml, 5 µg/ml), ADP (10 µM) and thrombin (0.5 U/ml).

2. Results: Effect of test compounds is indicated in the following table (1) against collagen and epinephrine induced thrombosis in mice, which is a primary screening model to detect antithrombotic efficacy of the test agents. At the same dose these compounds were also evaluated for their effect on the bleeding time in mouse (Table 1).

Since compound (i), (ii) and (iii) exhibited significant protection these compounds were further analysed in greater details for the anti-thrombotic activity in various test systems, as indicated below.

Effect on venous thrombosis model in rabbit: The selected compounds were evaluated at 10 µM/Kg and 30 µM/kg dose for their efficacy against stasis induced thrombosis in LPS treated rabbits. (i) was found to be most effective as it inhibited thrombus formation significantly it both 30 and 10 μM/Kg, while n and a inhibited thrombus formations only at 30 μM/Kg. heparin was used a standard drug in this model and the results obtained are shown in the Table 2.

Ex vivo effect of selective compounds on rat platelet aggregation: Blood was collected in sodium citrate to obtain PRP and evaluate the ex vivo effect of selective compounds ((i), (ii), (iii) at 30 μM/kg administered by the ip route) against ADP, collagen, phorbol myristate ester (PMA) calcium ionophore (A23187), or thrombin induced aggregation. It was observed that all these compounds were consistent against collagen-induced platelet aggregation (Table 3). (iii) inhibited ADP (10 μM), collagen (10 μg/ml), PMA (1.5 μM), and thrombin (0.64 U/ml) induced platelet aggregation while no inhibition was found against calcium ionophore A23187 (2.5 μg/ml) induced platelet aggregation. Compound (ii) inhibited only ADP (10 μM), collagen (10 μg/ml), PM (1.5 μM), and A23187 (2.5 μg/ml) induced platelet aggregation however it did not inhibit thrombin (0.64 U/ml) induced platelet aggregation Compound (i) inhibited ADP (10 μM), collagen (10 μg/ml), and A23187 (2.5 μg/ml) induced platelet aggregation but bad no inhibitory effect against thrombin (0.64 U/ml) and PMA (1.5 μM) induced platelet aggregation.

Effect on clotting parameters: The selected compounds were also tested in vitro for their effect on thrombin time (TT), prothrombin time (PT) and activated partial thromboplastin time (aPTT) at 100 μg/ml and 200 μg/ml in vitro (Table 4). The test compounds at 100 μg/ml had no significant effect of on these parameters. Some effect was though seen on PT at 200 μg/ml concentration, but the concentration seems to be quite high.

Figure 1:
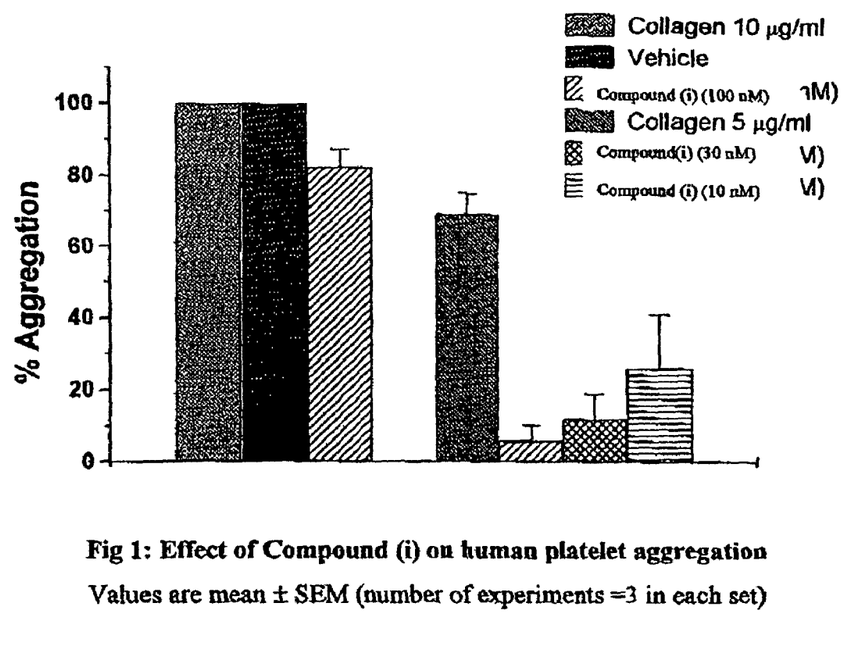
FIG. 1 is a graphical representation of the effect of compound (i) on human platelet aggregation.

Effect of compound (i) on human platelet aggregation in human PRP in vitro: Since the compound (i) exhibited promising profile against venous thrombosis model in rabbits as well as in other test systems; it was therefore further studied for inhibition of aggregation in human platelet rich plasma (PRP). It was found to be a competitive inhibitor of collagen induced platelet aggregation, collagen (10 μg/ml) induced aggregation was not so significantly reduced in presence of compound (i), while response of low concentration of collagen (5 μg/ml) was reduced significantly (FIG. 1).

TABLE 1

Antithrombotic Effect of the test compounds on mice model and bleeding time

| Sl no. | Compound No. (dose 30 μM/kg) | Antithrombotic activity (AT) (% protection) | Bleeding time (BT) % increase (1 hr) |
|---|---|---|---|
| | Control | 0 | — |
| 1 | A Compound(i) | 60 ± 10 (n = 4) | 51 ± 14 (n = 5) |
| 2 | b | 20 | 31 |
| 3 | c | 0 | 18 |
| 4 | d | 20 | 0 |
| 5 | e | 0 | 13 |
| 6 | f | 20 | 25 |
| 7 | g | 20 | 0 |
| 8 | h | 0 | 0 |
| 9 | i | 0 | 0 |
| 10 | j | 56 | 150 |
| 11 | k | 50 | 0 |
| 12 | o | 40 | 31 |
| 13 | p Compound(ii) | 70 ± 10 (n = 3) | 33 ± 12 (n = 3) |
| 14 | q | 20 | 12 |
| 15 | r | 30 | 0 |
| 16 | s | 60 | 13 |
| 17 | t | 30 | 0 |
| 18 | u | 45 | 0 |
| 19 | v | 30 | 50 |
| 20 | w Compound(iii) | 70 ± 0 (n = 3) | 61 ± 16 (n = 3) |
| | Aspirin (30 mg/Kg) | 38 ± 3 (n = 24) | 125 ± 6 (n = 30) |
| | Indomethacin (10 mg/kg) | 55 ± 15 (n = 20) | — | n = number of groups

Number of mice used for AT testing were 10 in each group, while 5 mice were used in each group to evaluate BT. Values are mean±SEM.

TABLE 2

Effect of Test compounds on venous thrombosis model in rabbits:

| Test compounds | 10 μM/Kg dose | | 30 μM/Kg dose | | | |
|---|---|---|---|---|---|---|
| | Thrombus wt. | % Reduction | Thrombus wt. | % Reduction | Thrombus wt. | % Reduction |
| Control | 43 ± 13 | | | | | |
| (i) | 26 ± 0 | 41 | 0.0 ± 0.0 | 100.0 | | |
| (ii) | 79 ± 9 | −67 | 5 ± 4 | 88 | | |
| (iii) | — | — | 11 ± 5 | 57 | | |
| Heparin | 0.5 mg/Kg dose | | 0.25 mg/Kg dose | | 0.1 mg/Kg dose | |
| | 1 ± 0.2 | 98 | 2 ± 0.3 | 95 | 4 ± 0.5 | 91 |

Values are Mean±; Compound (i); n=2, Compound (ii); n=4, Compound (iii), n=4 [n is no. of observations in 2 or more animals at 10 μM/Kg or 30 μM/Kg p.o. administered 2 h prior to the stasis] or vehicle control [n=10 observations in five animals]. In heparin treated group n=6 observations for each dose in nine animals.

TABLE 3

Effect of Test compounds on the platelet aggregation

| Aggregation Inducers | Compound(i) % Aggregation | Compound(i) % Inhibition | Compound(ii) % Aggregation | Compound(ii) % Inhibition | Compound(iii) % Aggregation | Compound(iii) % Inhibition |
|---|---|---|---|---|---|---|
| ADP (10 μM) | 37 ± 4 n = 12 | 17 ± 6 n = 12 | 35 ± 5 n = 8 | 26 ± 10 n = 8 | 2 ± 0.4 n = 4 | 94 ± 0.2 n = 4 |
| Thrombin (0.64 U/ml) | 45 ± 4 n = 10 | −9 ± 9 n = 10 | 44 ± 10 n = 4 | 4 ± 10 n = 4 | 28 ± 3 n = 6 | 40 ± 6 n = 6 |
| Collagen (10 μg/ml) | 22 ± 9 n = 8 | 65 ± 13 n = 8 | 5 ± 1 n = 4 | 79 ± 7 n = 4 | 2.5 ± 0 n = 2 | 47 ± 13 n = 2 |
| A23187 (2.5 μg/ml) | 51 ± 4 n = 8 | 11 ± 4 n = 8 | 51 ± 5 n = 6 | 54 ± 4 n = 6 | 57 ± 6 n = 4 | −25 ± 2 n = 4 |
| PMA (1.5 μM) | 58 ± 6 n = 6 | −12 ± 9 n = 6 | 44 ± 12 n = 2 | 26 ± 0.3 n = 2 | 38 ± 13 n = 2 | 32 ± 5 n = 2 | n = number of experiments which consists of at least 6 or more observations

TABLE 4

Effect of test substances against clotting parameters

| | Compound (i) | Compound (ii) | Compound (iii) | Conc. (μg/ml) |
|---|---|---|---|---|
| | % Change | | | |
| Thrombin time (TT) | 5 ± 5 | 9 ± 5 | 10 ± 4 | 100 |
| | 9 ± 5 | 9 ± 4 | 6 ± 1 | 200 |
| Prothrombin time (PT) | 19 ± 16 | 9 ± 5 | −0.24 ± 0.8 | 100 |
| | 14 ± 3 | 14 ± 7 | 9 ± 0.2 | 200 |
| Activated partial thromboplastin time (aPTT) | 7 ± 5 | 13 ± 7 | 11 ± 4 | 100 |
| | 4 ± 3 | 11 ± 4 | 10 ± 8 | 200 |

Values are mean ± SEM (number of observation [n] = 3 in each case)

The following examples are provided by the way of illustration of the present invention.

EXAMPLE 1

Preparation of 2-[-2,5dichlorobenzenesulfonyl]-1,2,3,4,-tetrahydro-9H-pyrido[3,4-b]indole-3-carboxylic acid ester.

i) 2,5 dichlorobenzene sulphonyl chloride (0.541 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stir for 10 hrs. at room temperature (32° C.). The reaction mixture was concentrated under vaccum, the residue was triturated with water (20 ml) to get 2-[2,5-dichlorobenzenesulfonyl]-1,2,3,4,-tetrahydro-9H-pyrido[3,4-b]indole-3-carboxylic acid ester, crystallized with methanol, Yield=0.650 gm (74.031%). m.p.=205° C. Mass (FAB) m/z=440 (M$^+$). IR(KBrcm$^{-1}$): 3412, 1730, 1600, 1446, 1343, 1271, 1162, 738. $^1$HNMR (200 MHz, CDCl$_3$): δ 3.14-3.38 (m, 2H), δ 3.61 (s, 3H, δ 4.67-4.88 (m, 2H), δ 5.19 (d, 1H), δ 7.08-7.21 (m, 2H), δ 7.44-7.49 (m, 3H), δ 7.79 (d, 1H) δ 8.16 (s, 1H). Molecular Formula=$C_{19}H_{16}Cl_2N_2O_4S$.

EXAMPLE 2

Preparation of 2-[2,4,6, trimethyl benzenesulfonyl]-1,2,3,4,-tetrahydro-9H-pyrido[3,4-b]indole-3-carboxylic acid ester.

i) 2,4,6,trimethyl benzene sulphonyl chloride (0.479 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stir for 8 hrs. at room temperature (32° C.). The reaction mixture was concentrated under vaccum, the residue was rated with water (20 ml) to get 2-[2,4,6,trimethylbenzenesulfonyl]-1,2,3,4,-tetrahydro-9H-pyrido[3,4-b]indole-3-carboxylic acid ester, crystallized with methanol. Yield=0.521 gm (63.21%), m.p.=160° C. Mass (FAB): m/z=413 (M$^+$). IR (KBr cm$^{-1}$): 3400, 2938, 1734, 1599, 1452, 1330, 1237, 1153, 738. $^1$HNMR (200 MHz, CDCl$_3$): δ 2.29 (s, 3H), δ2.63 (s, 6H), δ3.05-3.39 (m, 2H), δ3.64 (s, 3H), δ4.50 (d, 1H), δ4.79-4.93 (m, 2H), δ6.95 (s, 2H), δ7.05-7.20 (m, 2H), δ7.45 (d, 1H), δ7.78 (s, 1H). Molecular Formula=$C_{22}H_{24}N_2O_4S$.

EXAMPLE 3

Preparation of 2[2,nitrobenzenesulfonyl]-1,2,3,4,-tetrahydro-9H-pyrido[3,4-b]indole-3-carboxylic acid ester.

i) 2-nitrobenzenesulphonyl chloride (0.486 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2 mmol) and dry triethylamine (0.56 ml, 4.0 mmol) in dry acetone (8 ml) during 15 min and was allowed to stir for 8 hours at room temperature (32° C.). The reaction mixture was concentrated under vaccum, the residue was triturated with water (20 ml) to get 2-[2,nitrobenzenesulfonyl]-1,2,3,4,-tetrahydro-9H-pyrido[3,4-b]indole-3-carboxylic acid ester, crystallized with methanol, Yield=0.42 gm (50.6%), m.p.=225-230° C. Mass (FAB) m/z=416 (M$^+$). IR (KBr cm$^{-1}$): 3424, 1743, 1598, 1363, 1229, 1166, 753. $^1$HNMR (200 MHz, CDCl$_3$): δ 3.16-3.44 (m, 2H), δ3.55 (s, 3H), δ4.83 (s, 2H), δ5.20 (d, 1H), δ7.04-7.19 (m, 2H), δ 7.33 (d, 1H), δ 7.45-7.47 (m, 1H), δ7.69-7.79 (m, 3H), δ 8.10-8.18 (m, 1H). Molecular Formula=$C_{19}H_{17}N_3O_6S$.

EXAMPLE 4

Preparation of 2[1-naphthylsulfonyl]-1,2,3,4,-tetrahydro-9H-pyrido[3,4-b]indole-3-carboxylic acid ester.

i) 1-naphthylsulfonyl chloride (0.497 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stir for 8 hrs. at room temperature (32° C.). The reaction mixture was concentrated under vacuum, the residue was triturated with water (20 ml) to get 2-[1-naphthylsulfonyl]-1,2,3,4,-tetrahydro-9H-pyrido[3,4-b]indole-3-carboxylic acid ester, crystallized with methanol, Yield=0.55 gm (65%), m.p.=215° C. Mass (AB) m/z=421 (M$^+$) IR (KBr cm$^{-1}$): 3402, 1736, 1596, 1447, 1325, 1236, 1200, 1163, 733. $^1$HNMR (200 MHz, CDCl$_3$): δ 3.09-3.29 (m, 1H), δ 3.35-3.40 (m, 4H), δ 4.76 (s, 2H), δ 5.28 (d, 1H), δ 7.03-7.19 (m, 2H), δ 7.40-7.70 (m, 5H), δ 7.90 (d, 1H), δ 8.06 (d, 1H), δ 8.30 (d, 1H), δ 8.68 (d, 1H). Molecular Formula=$C_{23}H_{20}N_2O_4S$.

EXAMPLE 5

Preparation of 2-[4-methoxybenzenesulfonyl]-1,2,3,4,-tetrahydro-9H-pyrido[3,4-b]indole-3carboxylic acid ester.

i) 4-methoxy benzene sulphonyl chloride (0.453 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stir for 8 hours at room temperature (32° C.). The reaction mixture was concentrated under vaccum, the residue was triturated with water (20 ml) to get 2-[4-methoxybenzenesulfonyl]-1,2,3,4,-tetrahydro-9H-pyrido[3,4-b]indole-3-carboxylic acid ester, crystallized with methanol, Yield=0.682 gm (85.25%) m.p.=215° C. Mass (FAB) m/z=401 (M$^+$). IR (KBr cm$^{-1}$) 3426, 1748, 1594, 1450, 1344, 1256, 1155, 741. $^1$HNMR (200 MHz, CDCl$_3$): δ 3.05-3.37 (m, 2H), δ 3.47 (s, 3H), δ 3.84 (s, 3H), δ 4.59-4.86 (m, 2H), δ5.16 (d, 1H), δ 6.92-7.46 (m, 5H), δ7.82 (d, 3H). Molecular Formula=$C_{20}H_{20}N_2O_5S$.

EXAMPLE 6

Preparation of 2-[8-quinolinesulfonyl]-1,2,3,4,-tetrahydro-9H-pyrido[3,4-b]indole-3-carboxylic acid ester.

i) 8-quinolinesulphonylchloride (0.499 gm, 2.2 mmol) in dry acetone (5ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stirr for 8 hours at room temperature (32° C.). The reaction mixture was concentrated under vaccum, the residue was triturated with water (20 ml) to get 2-[8-quinolinesulfonyl]-1,2,3,4,-tetrahydro-9H-pyrido[3,4-b]indole-3-carboxylic acid ester, crystallized with methanol, Yield=0.619 gm (73.6%) m.p.=235° C. Mass (FAB) m/z=422 (M$^+$). IR (KBr cm$^{-1}$) 3400, 1733, 1621, 1564, 1446, 1327, 1213, 1161, 743. $^1$HNMR (200 MHz CDCl$_3$): δ2.99-3.10 (m, 1H), δ 3.31-3.44 (m, 4H), δ 4.80-5.01 (m, 2H), δ 5.78 (d, 1H), δ 7.00-7.18 (m, 2H), δ7.39-7.49 (m, 2H), δ7.60-δ67.80 (m, 2H), δ 8.02(d, 1H), δ6.20 (d, 1H), δ8.56 (d, 1H), δ9.00 (d, 1H). Molecular Formula=$C_{22}H_{19}N_3O_4S$.

EXAMPLE 7

Preparation of 2-[dansylsulfonyl]-1,2,3,4,-tetrahydro-9H-pyrido[3,4-b]indole-3-carboxylic acid ester.

i) 2-dansylsulphonylchloride (0.592 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stir for 8 hrs. at room temperature (32° C.). The reaction mixture was concentrated under vaccum, the residue was triturated with water (20 ml) to get 2-[dansylsulfonyl]-1,2,3,4,-tetrahydro-9H-pyrido[3,4-b]indole-3-carboxylic acid ester, crystallized with acetone, Yield=0.364 gm (44.9%) m.p.=195° C. Mass (FAB) m/z=464 (M$^+$). IR (KBr cm$^{-1}$) 3407, 1741, 1595, 1451, 1345, 1201, 1151, 744. $^1$HNMR (200 MHz, CDCl$_3$) δ 2.85 (s, 6H), δ 3.08-3.18 (m, 1H), δ 3.33-3.45 (m, 4H), δ 4.71-4.77 (m, 2H), δ 5.28 (d, 1H), δ 7.10-7.16 (m, 3H), δ 7.39-7.58 (m, 3H), δ 7.75 (s, 1H), δ 8.29 (d, 2H), δ 8.51 (d, 1H). Molecular Formula=$C_{25}H_{25}N_3O_4S$.

EXAMPLE 8

Preparation of 2-[2,4,6triisopropylbenzenesulfonyl]-1,2,3,4,-tetrahydro-9H-pyrido[3,4-b]indole-3-carboxylic acid ester.

i) 2,4,6triisopropylbenzenesulphonyl chloride (0.664 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stirr for 24 hrs. at room temperature (32° C.). The reaction mixture was concentrated under vaccum, the residue was triturated with water (20 ml) to get 2-[2,4,6triisopropylbenzenesulfonyl]-1,2,3,4,-tetrahydro-9H-pyrido[3,4-b]indole-3-carboxylic acid ester, crystallized with acetone, Yield=0.310 gm (31.25%). m.p.=200° C. Mass (FAB) m/z=497 (M$^+$). IR (KBr cm$^{-1}$): 3408, 2960, 1744, 1626, 1457, 1317, 1160, 1040, 934, 746. $^1$HNMR (200 MHz, CDCl$_3$) δ1.20-1.33 (m, 18H), δ2.81-2.98 (m, 1H), δ3.10-3.40 (m, 2H), δ3.65 (s, 3H), δ4.05-4.19 (m, 2H), δ 4.45 (d, 1H), δ 4.88 (d, 1H), δ 5.12 (d, 1H), δ 7.05-7.17 (m, 4H), δ7.46 (d, 1H), δ 7.80 (s, 1H). Molecular Formula=$C_{28}H_{36}N_2O_4S$.

EXAMPLE 9

Preparation of 2-[4-fluorobenzenesulfonyl]-1,2,3,4,-tetrahydro-9H-pyrido[3,4-b]indole-3-carboxylic acid ester.

) 4-fluorobenzenesulfonyl chloride (0.427 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone, (8 ml) during 15 min and was allowed to stir for 8 hrs. at room temperature (32° C.). The reaction mixture was concentrated under vacuum, the residue was triturated with water (20 ml) to get 2-[4-fluorobenzenesulfonyl]-1,2,3,4,-tetrahydro-9H-pyrido[3,4-b]indole-3-carboxylic acid ester, crystallized with acetone, Yield=0.666 gm (67.19%) m.p.=190° C. Mass (FAB) m/z=389 (M$^+$). IR (KBr cm$^{-1}$) 3430, 1748, 1591, 1489, 1344, 1228, 1156, 742. $^1$HNMR (200 MHz, CDCl$_3$) δ 3.08-3.19 (m, 1H), δ 3.32-3.47 (m, 4H), δ 4.59-4.88 (m, 2H, δ 5.16 (d, 1H), δ 7.10-7.32 (m, 4H), δ 7.45 (d, 1H), δ7.83-7.90 (m, 3H). Molecular Formula=$C_{19}H_{17}FN_2O_4S$.

EXAMPLE 10

Preparation of 2-[2-trifluoromethylbenzenesulfonyl]-1,2,3,4,-tetrahydro-9H-pyrido[3,4-b]indole-3-carboxylic acid ester.

i) 2-trifluoromethylbenzenesulfonyl chloride (0.537 gm, 2.2 mmol) in dry acetone, (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stir for 8 hrs. at room temperature (32° C.). The reaction mixture was concentrated under vacuum, the residue was triturated with water (20 ml) to get 2-[2-trifluoromethylbenzenesulfonyl]-1,2,3,4,-tetrahydro-9H-pyrido[3,4-b]indole-3-carboxylic acid ester, crystallized with acetone, Yield=0.524 gm (59.8%), m.p.=136° C. Mass (FAB) m/z=439 (M$^+$) IR (KBr cm$^{-1}$) 3400, 1741, 1563, 1449, 1347, 1308, 1272, 1218, 1169, 771. $^1$HNMR (200 MHz, CDCl$_3$): δ 3.18-3.24 (m, 1H), δ 3.40-3.50 (m, 1H, δ 3.56 (s, 3H), δ 4.75 (s, 2H), δ 5.20 (d, 1H), δ 7.11-7.15 (m, 2H), δ 7.46-7.49 (d, 1H), δ 7.68-7.91 (m, 4H), δ 8.21-8.24 (m, 1H). Molecular Formula=$C_{20}H_{17}F_3N_2O_4S$.

EXAMPLE 11

Preparation of 2-[methanesulfonyl]-1,2,3,4,-tetrahydro-9H-pyrido[3,4-b]indole-3-carboxylic acid ester.

i) Methane sulphonyl chloride (0.18 ml, 24 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stirr for 8 hrs. at room temperature (32° C.). The reaction mixture was concentrated under vaccum, the residue was triturated with water (20 ml) to get 2-[methyl sulfonyl]-1,2,3,4,-tetrahydro-9H-pyrido[3,4-b]indole-3-carboxylic acid ester, crystallized with acetone. Yield=0.480 gm (77.9%), m.p.=198° C. Mass (FAB) m/z=309 (M$^+$). IR (KBr cm$^{-1}$), 3384, 3026, 1736, 1632, 1278, 1234, 1152, 1016, 746. $^1$HNMR (200 MHz, Acetone): δ 2.91 (s, 3H), δ 2.97-3.35 (m, 2H), δ3.51 (s, 3H), δ 4.52-4.74 (m, 2H), δ 4.99 (d, 1H), δ6.85-7.00 (m, 2H), δ7.22 (d, 1H), δ 7.34 (d, 1H), δ10.00 (s, 1H). Molecular Formula=$C_{14}H_{16}N_2O_4S$.

EXAMPLE 12

Preparation of 2-[2-naphthalenesulfonyl]-1,2,3,4,-tetrahydro-9H-pyrido[3,4-b]indole-3-carboxylic acid ester.

i) 2-naphthylsulphonyl chloride (0.497 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (10 ml) during 15 min and was allowed to stir for 12 hours at room temperature 32° C. The reaction mixture was concentrated under vacuum, the residue was triturated with water (20 ml) to give 2-[2-naphthalenesulfonyl]-1,2,3,4,-tetrahydro-9H-pyrido[3,4-b]indole-3-carboxylic acid ester, crystallized with methanol, Yield=0.714 gm (85%). m.p.=210° C. Mass (FAB) m/z=421 (M$^+$). IR(KBrcm$^{-1}$): 3418, 1748, 1594, 1451, 1362, 1158, 751. $^1$HNMR (200 MHz, CDCl$_3$): δ 3.08-3.36 (m, 5H), δ 4.68-4.95 (m, 2H), δ 5.24 (d, 1H), δ 7.05-7.18 (m, 2H), δ 7.42 (d, 1H), δ 7.60-7.63 (m, 2H), δ 7.77-7.98 (m, 5H), δ 8.45 (s, 1H). Molecular Formula=$C_{23}H_{20}N_2O_4S$.

ii) 2-naphthylsulphonyl chloride (0.272 gm, 1.2 mmol) in dry acetone (3 ml) was added to a stirred solution of dl methyl-1,2,3,4-tetrahydro-9H-pyrido(3,4-b)indole-3-carboxylate (0.23 gm, 1.0 mmol) and dry pyridine (0.97 ml, 1.2 mmol) in dry acetone (10 ml) during 15 min and was allowed to stir for 12 hours at room temperature (32° C.). The reaction mixture was concentrated under vacuum, water (10 ml) was added to the residue and extracted with chloroform (3×10 ml). The extract was dried over Na$_2$SO$_4$ and concentrated over reduced pressure to give 2-[2-naphthalenesulfonyl]-1,2,3,4,-tetrahydro-9H-pyrido[3,4-b]indole-3-carboxylic acid ester, crystallized with methanol, Yield=0.227 gm (54%), m.p.=210° C.

iii) 2-naphthyl sulphonyl chloride (0.272 gm, 1.2 mmol) in dry acetone (3 ml) was added to a stirred solution of dl methyl-1,2,3,4-tetrahydro-9H-pyrido(3,4-b)indole-3-carboxylate (0.23 gm, 1.0 mmol) and K$_2$CO$_3$ (0.13 gm, 1.2 mmol) in dry acetone (10 ml) during 15 min and was allowed to stir for 8 hrs. at room temperature (32° C). The reaction mixture was concentrated under vacuum, water (10 ml) was added to the residue and extracted with chloroform (3×10 ml). The exact was dried over Na$_2$SO$_4$ and concentrated over reduced pressure to give 2-[2-naphthalenesulfonyl]-1,2,3,4,-tetrahydro-9H-pyrido[3,4-b]indole-3-carboxylic acid ester, crystallized with methanol. Yield=0.29 gm. (68%) m.p=210° C.

iv) 2-naphthyl sulphonyl chloride (0.272 gm, 1.2 mmol) in dry acetone (3 ml) was added to a stirred solution of dl methyl-1,2,3,4-tetrahydro-9H-pyrido(3,4-b)indole-3-carboxylate (0.23 gm, 1.0 mmol) and dry triethylamine (0.12 ml, 1.2 mmol) in THF (5 ml) during 15 min and was allowed to stir for 8 hours at room temperature (32° C.). The reaction mixture was concentrated under vacuum, the residue was triturated with water (20 ml) to give 2-[2-naphthalenesulfonyl]-1,2,3,4,-tetrahydro-9H-pyrido[3,4-b]indole-3-carboxylic acid ester, crystallized with methanol, Yield=0.32 gm. (75%), m.p: 210° C.

v) 2-naphthyl sulphonyl chloride (0.272 gm, 1.2 mmol) in dry acetone (3 ml) was added to a stirred solution of dl methyl-1,2,3,4-tetrahydro-9H-pyrido(3,4-b)indole-3-carboxylate (0.23 gm, 1.0 mmol) and dry triethylamine (0.12 ml, 1.2 mmol) in DMF (3 ml) during 15 min and was allowed to stir for 8 hours at room temperature (32° C). The reaction mixture was concentrated under vacuum, the residue was triturated with water (10 ml) then extracted with chloroform (3×10 ml). The extract was dried over Na₂SO₄ and concentrated over reduced pressure to give 2-[2-naphthalenesulfonyl]-1,2,3,4,-tetrahydro-9H-pyrido[3,4-b]indole-3-carboxylic acid ester, crystallized with methanol, Yield=0.21 gm. (50%), m.p: 210° C.

vi) 2-naphthyl sulphonyl chloride (0.272 gm, 1.2 mmol) in dry acetone (3 ml) was added to a stirred solution of dl methyl-1,2,3,4-tetrahydro-9H-pyrido(3,4-b)indole-3-carboxylate (0.23 gm, 1.0 mmol) and dry triethylamine (0.12 ml, 1.2 mmol) dry dioxane (5 ml) during 15 min and was allowed to stir for 8 hours at room temperature (32° C). Water (10 ml) was added to the residue and extracted with chloroform (3×10 ml). The extract was dried over Na₂SO₄ and concentrated over reduced pressure to give 2-[2-napthalenesulfonyl]-1,2,3,4,-tetrahydro-9H-pyrido[3,4-b]indole-3-carboxylic acid ester, crystallized with methanol, Yield=0.29 gm (70%), m.p: 210° C.

vii) 2-naphthyl sulphonyl chloride (0.272 gm, 1.2 mmol) in dry THF (3 ml) was added to a stirred solution of dl methyl-1,2,3,4-tetrahydro-9H-pyrido(3,4-b)indole-3-carboxylate (0.23 gm, 1.0 mmol) and K₂CO₃ (0.13 gm, 1.2 mmol) in dry THF and was allowed to stir for 12 hours at 80° C. temperature. The reaction mixture was concentrated under vacuum, water (8 ml) was added to the residue and extracted with chloroform (3×5 ml). The extract was dried over Na₂SO₄ and concentrated over reduced pressure to give 2-[2-naphthalenesulfonyl]-1,2,3,4,-tetrahydro-9H-pyrido[3,4-b]indole-3-carboxylic acid ester which was purified by column chromatography over silica gel using methanol chloroform as eluent Yield=0.20 gm (48%), m.p: 210° C.

viii) 2-naphthyl sulphonyl chloride (0.272 gm, 1.2 mmol) in dry DMF (3 ml) was added to a stirred solution of dl methyl-1,2,3,4-tetrahydro-9H-pyrido(3,4-b)indole-3-carboxylate (0.23 gm, 1.0 mmol) and K₂CO₃ (0.13 gm, 1.2 mmol) in dry DMF and was allowed to stir for 8 hours at 120° C. temperature. The reaction mixture was concentrated under vacuum, water (8 ml) was added to the residue and extracted with chloroform (3×8 ml). The extract was dried over Na₂SO₄ and concentrated over reduced pressure to give 2-[2-naphthalenesulfonyl]-1,2,3,4-tetrahydro-9H[3,4-b]indole-3-carboxylic acid ester which was purified by column chromatography over silica gel using methanol chloroform as eluent. Yield=0.170 gm (40%), m.p: 210° C.

EXAMPLE 13

2[benzenesulfonyl]-1,2,3,4,-tetrahydro-9H-pyrido[3,4-b]indole-3-carboxylic acid ester i) Benzene sulphonyl chloride (0.388 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stir for 8 hrs. at room temperature (32° C.). The reaction mixture was concentrated under vaccum, the residue was triturated with water (20 ml) to get 2-[benzenesulfonyl]-1,2,3,4,-tetrahydro-9H-pyrido[3,4-b]indole-3-carboxylic acid ester, crystallized with acetone. Yield=0.371 gm (50%), m.p.=124° C. Mass (FAB) m/z=371 (M⁺). IR (KBr cm⁻¹): 3838, 3024, 1742, 1442, 1342, 1052, 746. ¹HNMR (200 MHz, CDCl₃): δ3.04-3.42 (m, 5H), δ 3.30-3.42 (m, 4H), δ4.61-4.89 (m, 2H), δ5.16 (d, 1H), δ7.05-7.19 (m, 2H), δ7.42-7.60 (m, 4H), δ7.83-7.91 (m, 3H). Molecular Formula=C₁₉H₁₈N₂O₄S.

EXAMPLE 14

2-[4-methylbenzenesulfonyl]-1,2,3,4,-tetrahydro-9H-pyrido[3,4-b]indole-3-carboxylic acid ester i) 4-methyl benzene sulphonyl chloride (0.419 gm, 2.2 mmol) in dry acetone (5 ml) was added to a stirred solution of dl methyl-1,2,3,4-tetrahydro-9H-pyrido(3,4-b)indole-3-carboxylate (0.46 gm, 2.0 mmol) and dry triethylamine (0.56 ml, 4.0 mmol) in dry acetone (8 ml) during 15 min and was allowed to stirr for 8 hrs. at room temperature (32° C.). The reaction mixture was concentrated under vaccum, the residue was triturated with water (20 ml) to get 2-[4-methylbenzenesulphonyl]-1,2,3,4,-tetrahydro-9H-pyrido[3,4-b]indole-3-carboxylic acid ester, crystallized with acetone. Yield=0.400 gm (51%), m.p.=128° C. Mass (FAB) m/z=385 (M⁺). IR (KBr cm⁻¹): 3427, 1744, 1597, 1445, 1337, 1159, 1091, 1051, 1016, 935, 746. ¹HNMR (200 MHz CDCl₃): δ2.40 (s, 3H), δ3.05-3.45 (m, 5H), δ4.60-4.87 (m, 2H), δ5.15 (d, 1H), δ6.96-7.46 (m, 5H), δ7.70-7.85 (m, 3H). Molecular Formula=C₂₀H₂O₄S.

EXAMPLE 15

Preparation of 2-[2,5dichlorobenzenesulfonyl]-1,2,3,4,-tetrahydro-9H-pyrido[3,4-b]indole-3-carboxylic acid amide i) 2,5 dichlorobenzene benzene sulphonyl chloride (0.590 gm, 2.4 mmol) in dry acetone (5 ml) was added to a stirred solution of dl 1,2,3,4-tetrahydro-9H-pyrido(3,4-b)indole-3-amide (0.430 gm, 1.0 mmol) and dry triethylamine (0.56 ml, 4.0 mmol) in dry DMF (5 ml) during 15 min and was allowed to stir for 8 hrs. at room temperature (32° C.). Water was added to the reaction mixture and triturated to give 2-[2,5dichlorobenzene benzene sulfonyl]-1,2,3,4,-tetrahydro-9H-pyrido[3,4-b]indole-3-carboxylic acid amide which was purified by column chromatography over silica gel using 2% methanol chloroform as eluent. Yield=0.400 gm (47.17%)

ii) 2-2,5 dichlorobenzene sulfonyl]-1,2,3,4,-tetrahydro-9H-pyrido[3,4-]indole-3-carboxylic acid ester (0.220 gm, 0.5 mmol) was kept at room temperature (32° C.) in methanolic ammonia (25 ml) for 32 hours The reaction mixture was then evaporated under vaccum to obtain to obtain 2-[2,5dichlorobenzenesulfonyl]-1,2,3,4,-tetrahydro-9H-pyrido[3,4-b]indole-3-carboxylic acid amide, crystallized in methanol chloroform solution (2:1). Yield=0.185 gm (87.26%). m.p.=220° C. Mass (FAB) m/z=425 (M⁺). IR (KBr cm⁻¹): 3456, 3332, 1693, 1602, 1450, 1337, 1160, 752. ¹HNMR (200 MHz, Acetone) δ 3.06-3.73 (m, 2H), δ 4.87 (s, 2H), δ4.97 (d, 1H), δ6.41 (s, 1H), δ7.01-6.84 (m, 3H), δ 7.32-7.21 (m, 2H), δ 7.60-7.48 (m, 2H), δ 8.08-8.67 (d, 1H), δ 9.95 (s, 1H). Molecular Formula=C₁₈H₁₅Cl₂N₃O₃S.

EXAMPLE 16

Preparation of 2-[4-methoxybenzenesulfonyl]-1,2,3,4,-tetrahydro-9H-pyrido[3,4-b]indole-3-carboxylic acid amide i) 4-methoxy benzene sulphonyl chloride (495 gm, 2.4 mmol) in dry acetone (5 ml) was added to a stirred solution of dl 1,2,3,4-tetrahydro-9H-pyrido(3,4-b)indole-3-amide (0.430 gm, 1.0 mmol) and dry triethylamine (0.56 ml, 4.0 mmol) in dry DMF (5 ml) during 15 min and was allowed to stirr for 8 hrs. at room temperature (32° C.). Water was added to the reaction mixture and triturated to give 2-[4-methoxybenzenesulfonyl]-1,2,3,4,-tetrahydro-9H-pyrido[3,4-b]indole-3-carboxylic acid amide, which was purified by column chromatography over silica gel using 2% methanol chloroform as eluent. Yield=0.480 gm, (62.34%). m.p.=178-180° C.

ii) 2-[4-methoxy benzene sulfonyl]-1,2,3,4,-tetrahydro-9H-pyrido[3,4-b]indole-3-carboxylic acid ester (0.200 gm, 0.5 mmol) was kept at room temperature (32° C.) in methanolic ammonia (30 ml) for 24 hrs. The reaction mixture was then evaporated under vaccum to obtain 2-[4methoxybenzenesulfonyl]-1,2,3,4,-tetrahydro-9H-pyrido[3,4-b]indole-3-carboxylic acid amide, crystallized in methanol (5 ml) Yield=0.170 gm (88%), m.p.=—178-180° C. Mass (FAB) m/z=386 (M$^+$). IR (KBr cm$^{-1}$): 3375, 1698, 1595, 1495, 1447, 1342, 1256, 1151, 756. $^1$HNMR (200 MHz, CDCl$_3$) δ 2.43-2.54 (m, 1H), δ3.43-3.77 (s, 4H), δ4.80-4.96 (m, 3H), δ6.81-6.86 (d, 2H), δ7.04-7.39 (m, 6H), δ7.67-7.72 (d, 2H). Molecular Formula=$C_{19}H_{19}N_3O_4S$.

EXAMPLE 17

Preparation of 2-[1-naphthylsulfonyl]-1,2,3,4,-tetrahydro-9H-pyrido[3,4-b]indole-3-carboxylic acid amide.

i) 2-[1-naphthylsulfonyl]-1,2,3,4,-tetrahydro-9H-pyrido[3,4-b]indole-3-carboxylic acid ester (0.210 gm, 0.5 mmol) was kept at room temperature (32° C.) in methanolic ammonia (30 ml) for 24 hrs. The reaction mixture was then evaporated under vacuum to obtain 2[-1-naphthylsulfonyl]-1,2,3, 4,-tetrahydro-9H-pyrido[3,4-b]indole-3-carboxylic acid amide, Yield=0.174 gm (85%). m.p.=145-150° C. Mass (FAB) m/z=406 (M$^+$). IR (KBr cm$^{-1}$) 3397, 1597, 1447, 1349, 1204, 1160, 799, 750. H$^1$NMR (200 MHz, CDCl$_3$): δ 2.60-2.72 (m, 1H), δ 3.56 (d, 1H), δ 4.60-5.00 (m, 3H), δ 5.39 (s, 1H), δ 6.61 (s, 1H), δ 7.03-7.49 (m, 7H), δ 7.88 (d, 1H), δ 8.06 (d, 1H), δ 8.30 (d, 1H), δ 8.50 (d, 1H). Molecular Formula=$C_{22}H_{19}N_3O_3S$.

EXAMPLE 18

Preparation of 2-[8-quinolinesulfonyl]-1,2,3,4,-tetrahydro-9H-pyrido[3,4-b]indole-3-carboxylic acid amide.

i) 2-[8-quinolinesulfonyl]-1,2,3,4,-tetrahydro-9H-pyrido[3,4-b]indole-3-carboxylic acid ester (0.211 gm, 0.5 mmol) was kept at room temperature (32° C.) in methanolic ammonia (30 ml) for 48 hrs. The reaction mixture was then evaporated under vaccum to obtain 2-[8-quinolinesulfonyl]-1,2,3, 4,-tetrahydro-9H-pyrido[3,4-b]indole-3-carboxylic acid amide. This was purified by column chromatography over silica gel using 2% methanol chloroform as eluent. Yield=0.130 gm (64.04%). m.p.=160° C. Mass (FAB) m/z=407 (M$^+$). IR (KBr cm$^{-1}$): 3426, 3338, 1686, 1617, 1493, 1450, 1328, 1161, 1139, 740. H$^1$NMR (200 MHz, CDCl$_3$) δ 2.33-2.45 (m, 1H), δ3.33-3.59 (m, 1H), δ5.16-5.48 (m, 3H), δ6.96-7.42 (m, 6H), δ7.61-7.83 (m, 2H), δ8.18-8.63 (m, 2H), δ8.56 (d, 1H), δ8.80-8.32 (d, 1H). Molecular Formula=$C_{21}H_{18}N_4O_3S$.

EXAMPLE 19

Preparation of 2-[4-fluorobenzenesulfonyl]-1,2,3,4,-tetrahydro-9H-pyrido[3,4-b]indole-3-carboxylic acid amide.

i) 2-[4-fluorobenzenesulfonyl]-1,2,3,4,-tetrahydro-9H-pyrido[3,4-b]indole-3-carboxylic acid ester (0.388 gm, 0.5 mmol) was kept at room temperature (32° C.) in methanolic ammonia (30 ml) for 24 hrs. The reaction mixture was then evaporated under vacuum to obtain 2-[4-fluorobenzenesulfonyl]-1,2,3,4,-tetrahydro-9H-pyrido[3,4-b]indole-3-carboxylic acid amide, Yield=0.300 gm (80.41%). m.p.=220° C. Mass (FAB) m/z=374 (M$^+$). IR (KBr cm$^{-1}$): 3461, 3371, 1690, 1598, 1488, 1454, 1330, 1167, 764. $^1$HNMR (200 MHz, MeOH) δ 2.69-2.80 (m, 1H), δ 2.86-2.99 (m, 1H), δ 4.66-5.05 (m, 3H), δ 6.89-7.07 (m, 2H), δ 7.14-7.31 (m, 5H), δ 7.85-7.98 (m, 3H). Molecular Formula=$C_{18}H_{16}FN_3O_3S$.

EXAMPLE 20

Preparation of 2-[methanesulfonyl]-1,2,3,4,-tetrahydro-9H-pyrido[3,4-b]indole-3-carboxylic acid amide.

i) Methane sulphonyl chloride (0.18 ml, 2.4 mmol) was added to a stirred solution of dl 1,2,3,4-tetrahydro-9H-pyrido (3,4-b)indole-3-amide (0.430 gm, 2.0 mmol) and dry triethylamine (0.56 ml, 4.0 mmol) in dry DMF (8 ml) during 15 min at room temperature 30° C. The reaction mixture was allowed to stirr for 8 hrs. at room temperature. Water (20 ml) was added to the reaction mixture and extracted with chloroform (3×15 ml). The extract was dried over Na$_2$SO$_4$ and concentrated over reduced pressure to give 2-[methanesulphonyl]-1,2,3,4, -tetrahydro-9H-pyrido[3,4-b]indole-3-carboxylic acid amide which was purified by column chromatography over silica gel using 2% methanol chloroform as eluent. Yield=0.150 gm (25.60%). m.p.=234° C. Mass (FAB) m/z=294 (M$^+$). IR (KBr cm$^{-1}$): 3483, 3361, 1685, 1610, 1446, 1325, 1148, 756. H$^1$NMR (200 MHz, CDCl$_3$) δ 3.04 (s, 3H), δ3.20-3.63 (m, 2H), δ4.69-4.84 (m, 3H), δ6.96-7.15 (m, 3H), δ7.32-7.53 (m, 3H), δ10.89 (s, 1H). Molecular Formula=$C_{13}H_{15}N_3O_3S$.

EXAMPLE 21

Preparation of 2-[3-nitrobenzenesulfonyl]-1,2,3,4,-tetrahydro-9H-pyrido[3,4-b]indole-3-carboxylic acid amide.

i) 3-nitro benzene sulphonyl chloride (0.53 gm, 2.4 mmol) in dry acetone was added to a stirred solution of dl 1,2,3,4-tetrahydro-9H-pyrido(3,4-b)indole-3-amide (0.430 gm, 2.0 mmol) and dry triethylamine (0.56 ml, 4.0 mmol) in dry DMF (8 ml) during 15 min and was allowed to sir for 8 hrs. at room temperature. The reaction mixture was allowed to stirr for 8hrs. at room temperature. Water (20 ml) was added to the reaction mixture and extracted with chloroform (3×15 ml). The extract was dried over Na$_2$SO$_4$ and concentrated over reduced pressure to give 2-[3-nitrobenzenesulfonyl]-1,2,3,4,-tetrahydro-9H-pyrido[3,4-b]indole-3-carboxylic acid amide which was purified by column chromatography over silica gel using 2% methanol chloroform as eluent. Yield=0.400 gm (50%). m.p.=252° C. Mass (FAB) m/z=401 (M$^+$). IR (KBr cm$^{-1}$): 3459, 3378, 1692, 1618, 1528, 1353, 11173, 760. H$^1$NMR (200MHz, CDCl$_3$+DMSO d$_6$): δ2.88 (m, 1H), δ3.33 (d, 1H), δ4.73 (d, 1H), δ4.93 (d, 1H), δ5.06 (d, 1H), δ6.41 (s, 1H), δ6.89-7.31 (m, 3H), δ7.63-7.71 (m, 3H), δ8.13-8.17 (d, 1H), δ8.30 (d, 1H), δ8.59 (d, 1H), δ 10.27 (s, 1H). Molecular Formula=$C_{18}H_{16}N_4O_5S$.

EXAMPLE 22

Preparation of 2-[2,4,6trimethylbenzenesulfonyl]-1,2,3,4,-tetrahydro-9H-pyrido[3,4-b]indole-3-carboxylic acid amide i) 2,4,6trimethyl benzene sulphonyl chloride (0.524 gm, 2.4 mmol) in dry acetone was added to a stirred solution of dl 1,2,3,4-tetrahydro-9H-pyrido(3,4-b)indole-3-amide (0.430 gm, 2.0 mmol) and dry triethylamine (0.56 ml, 4.0 mmol) in dry DMF (8 ml) during 15 and was allowed to stirr for 8 hrs. at room temperature. Water (20 ml) was added to the reaction mixture and extracted with chloroform (3×15 ml). The tract was dried over $Na_2SO_4$ and concentrated over reduced pressure to give 2-[2,4,6trimethylbenzenesulfonyl]-1,2,3,4,-tetrahydro-9H-pyrido[3,4-b]indole-3-carboxylic acid amide which was purified by column chromatography over silica gel using 2% methanol chloroform as eluent Yield=0.35 gm (44.08%) m.p.=212° C.: Mass (FAB) m/z=398 (M$^+$). IR (KBr cm$^{-1}$): 3394, 3299, 1668, 1596, 1455, 1324, 1155, 752. H$^1$NMR (200 MHz, DMSO d$_6$) δ 2.30 (s, 3H), δ2.56-2.74 (m, 7H), δ3.55-3.62 (d, 1H), δ4.49-4.70 (m, 3H), δ5.17 (s, 1H), δ5.49 (s, 1H), δ6.96-7.77 (m, 6H). Molecular Formula=$C_{21}H_{23}N_3O_3S$.

EXAMPLE 23

Preparation of 2-[2-naphthylsulfonyl]-1,2,3,4,-tetrahydro-9H-pyrido[3,4-b]indole-3-carboxylic acid amide.

i) 2-[2-naphthylsulfonyl]-1,2,3,4,-tetrahydro-9H-pyrido [3,4-b]indole-3-carboxylic acid ester (0.210 gm, 0.5 mol) was kept at room temperature (32° C.) in methanolic ammonia (30 ml) for 24 hrs. The reaction mixture was then evaporated under vacuum to obtain 2-[2-naphthylsulfonyl]-1,2,3,4,-tetrahydro-9H-pyrido[3,4-b]indole-3-carboxylic acid amideYield=0.142 gm (70%). m.p.=240° C. Mass (FAB) m/z 406 (M$^+$). IR (KBr cm$^{-1}$): 3489, 3372, 1694, 1604, 1444, 1328, 1160, 1078, 754. $^1$HNMR (200 MHz, Acetone): δ 3.17-3.28 (m, 2H), δ 4.67-4.99 (m, 3H), δ 6.35 (s, 1H), δ 6.76-6.91 (m, 3H), δ 7.11-7.16 (d, 2H), δ 7.48-7.55 (m, 2H), δ 7.67-7.97 (m, 4H), δ 8.40 (s, 1H), δ 9.86 (s, 1H). Molecular Formula=$C_{22}H_{19}N_3O_3S$.

REFERENCES

1. Diminno, G.; Silver, M. J. *J. Pharmacol. Exp. Ther.* 1983, 225, 57-60.
2. Dejna, E.; Collioni, A.; Quntana, A. *Thromb. Res.* 1979, 15, 191-197.
3. Dikshit, M.; Kumari, R.; Srimal, R. C. *J. Pharmacol. Exp. Ther.* 1993; 265, 1369-1373.
4. S. Batra, S.; Roy, A. K.; Patra, A.; Bhaduri, A. P.; Surin, W. R.; Raghavan, S. A. V.; Sharma, P.; Kapoor, K.; Dikshit, M. *Bioorg. Med. Chem.* 2004, 12, 2059-2077.
5. Berry, C. N.; Girard, D.; Girardot, C.; Lochot, S.; Lunven, C.; Visconte, C. S. *Thromb. Haemost.* 1996, 22, 233-241.
6. Herbert, J. M.; Bernat, A.; Dol, F.; Herault, J. P.; Crepon, B.; Lormeau, J. M. *J. Pharmacol. Exp. Ther.* 1996, 276, 1030-1038.

We claim:
1. A compound of formula 1:

Formula 1 wherein
R is selected from the group consisting of the methyl ester, —C(O)OCH$_3$, and the amide, —C(O)NH$_2$; and
R$_1$ is selected from the group consisting of
  (a) a C$_1$ to C$_{10}$ alkyl;
  (b) an aryl selected from the group consisting of:
    unsubstituted phenyl,
    phenyl substituted by a moiety selected from the group consisting of halogen, alkyl, and alkoxy,
    unsubstituted naphthyl,
    naphthyl substituted by dimethyl amino; and
  (c) quinoline provided that when R is —C(O)OCH$_3$, (b) is not tolyl an unsubstituted phenyl or a phenyl substituted by an alkyl.

2. The compound of claim 1 wherein said compound is 2[-2,5 dichlorobenzenesulfonyl]-1,2,3,4,-tetrahydro-9H-pyrido[3,4-b]indole-3-carboxylic acid methyl ester.

3. The compound wherein said compound is 2[2,4,6, trimethyl benzenesulfonyl]-1,2,3,4,-tetrahydro-9H-pyrido[3,4-b]indole-3-carboxylic acid methyl ester.

4. The compound wherein said compound is 2[2,nitrobenzenesulfonyl]-1,2,3,4,-tetrahydro-9H-pyrido[3,4-b]indole-3-carboxylic acid methyl ester.

5. The compound of claim 1 wherein said compound is 2[1-naphthylsulfonyl]-1,2,3,4,-tetrahydro-9H-pyrido[3,4-b] indole-3-carboxylic acid methyl ester.

6. The compound of claim 1 wherein said compound is 2-4-methoxy benzenesulfonyl]-1,2,3,4,-tetrahydro-9H-pyrido[3,4-b]indole-3-carboxylic acid methyl ester.

7. The compound of claim 1 wherein said compound is 2[8-quinolinesulfonyl]-1,2,3,4,-tetrahydro-9H-pyrido[3,4-b]indole-3-carboxylic acid methyl ester.

8. The compound of claim 1 wherein said compound is 2-[dansylsulfonyl]-1,2,3,4,-tetrahydro-9H-pyrido[3,4-b]indole-3-carboxylic acid methyl ester.

9. The compound wherein said compound is 2[2,4,6 triisopropylbenzenesulfonyl]-1,2,3,4,-tetrahydro-9H-pyrido[3,4-b]indole-3-carboxylic acid methyl ester.

10. The compound of claim 1 wherein said compound is 2[4-fluorobenzenesulfonyl]-1,2,3,4,-tetrahydro-9H-pyrido [3,4-b]indole-3-carboxylic acid methyl ester.

11. The compound of claim 1 wherein said compound is 2[2-trifloromethyl benzenesulfonyl]-1,2,3,4,-tetrahydro-9H-pyrido[3,4-b]indole-3-carboxylic acid methyl ester.

12. The compound of claim 1 wherein said compound is 2[methylsulfonyl]-1,2,3,4,-tetrahydro-9H-pyrido[3,4-b]indole-3-carboxylic acid methyl ester.

13. The compound of claim 1 wherein said compound is 2-[2-naphthalenesulfonyl]-1,2,3,4,-tetrahydro-9H-pyrido[3,4-b]indole-3-carboxylic acid methyl ester.

14. The compound of claim 1 wherein said compound is 2[benzenesulfonyl]-1,2,3,4,-tetrahydro-9H-pyrido[3,4-b]indole-3-carboxylic acid methyl ester.

15. The compound of claim 1 wherein said compound is 2[-2,5 dichlorobenzenesulfonyl]-1,2,3,4,-tetrahydro-9H-pyrido[3,4-b]indole-3-carboxylic acid amide.

16. The compound of claim 1 wherein said compound is 2[-4-methoxybenzenesulfonyl]-1,2,3,4,-tetrahydro-9H-pyrido[3,4-b]indole-3-carboxylic acid amide.

17. The compound of claim 1 wherein said compound is 2[-1-naphthylsulfonyl]-1,2,3,4,-tetrahydro-9H-pyrido[3,4-b]indole-3-carboxylic acid amide.

18. The compound of claim 1 wherein said compound is 2[8-quinolinesulfonyl]-1,2,3,4,-tetrahydro-9H-pyrido[3,4-b]indole-3-carboxylic acid amide.

19. The compound of claim 1 wherein said compound is 2[-4-fluorobenzenesulfonyl]-1,2,3,4,-tetrahydro-9H-pyrido[3,4-b]indole-3-carboxylic acid amide.

20. The compound of claim 1 wherein said compound is 2[methylsulfonyl]-1,2,3,4,-tetrahydro-9H-pyrido[3,4-b]indole-3-carboxylic acid amide.

21. The compound wherein said compound is 2[3-nitrobenzenesulfonyl]-1,2,3,4,-tetrahydro-9H-pyrido[3,4-b]indole-3-carboxylic acid amide.

22. The compound wherein said compound is 2[2,4,6 trimethylbenzenesulfonyl]-1,2,3,4,-tetrahydro-9H-pyrido[3,4-b]indole-3-carboxylic acid amide.

23. The compound of claim 1 wherein said compound is 2[2-naphthalenesulfonyl]-1,2,3,4,-tetrahydro-9H-pyrido[3,4-b]indole-3-carboxylic acid amide.

24. A pharmaceutical composition comprising a pharmaceutically effective amount of the compound of formula 1 wherein
R is selected from the group consisting of the methyl ester, —C(O)OCH$_3$, and the amide, —C(O)NH$_2$; and
R$_1$ is selected from the group consisting of
  (a) a C$_1$ to C$_{10}$ alkyl;
  (b) an aryl selected from the group consisting of:
    unsubstituted phenyl,
    phenyl substituted by a moiety selected from the group consisting of halogen, alkyl and alkoxy,
    unsubstituted naphthyl,
    naphthyl substituted by dimethyl amino; and
  (c) provided that when R is —C(O)OCH$_3$, (b) is not tolyl an unsubstituted phenyl or a phenyl substituted by an alkyl;
and a pharmaceutically acceptable carrier.

* * * * *